United States Patent
Kimura

(10) Patent No.: US 6,825,195 B2
(45) Date of Patent: Nov. 30, 2004

(54) FLUORESCENT GROUP-CONTAINING CARBODIIMIDE COMPOUND AND PROCESS FOR PRODUCING THE COMPOUND

(75) Inventor: Naoki Kimura, Chiba (JP)

(73) Assignee: Nisshinbo Industries, Inc., Tokyo (JP)

( * ) Notice: Subject to any disclaimer, the term of this patent is extended or adjusted under 35 U.S.C. 154(b) by 0 days.

(21) Appl. No.: 10/154,321

(22) Filed: May 21, 2002

(65) Prior Publication Data

US 2003/0073866 A1 Apr. 17, 2003

(30) Foreign Application Priority Data

May 31, 2001 (JP) ........................................ 2001-164905
Mar. 29, 2002 (JP) ........................................ 2002-95074

(51) Int. Cl.$^7$ ................. A61K 31/5375; C07D 209/04; C07D 413/12
(52) U.S. Cl. .................... 514/237.2; 514/414; 544/144; 548/455
(58) Field of Search .................... 544/144; 548/455; 514/237.2, 414

(56) References Cited

U.S. PATENT DOCUMENTS 5,105,010 A  4/1992  Sundararaman et al.

FOREIGN PATENT DOCUMENTS

| DE | 100 46 215 A1 | 4/2002 |
|---|---|---|
| JP | 6-271599 | 9/1994 |
| JP | 10-287870 | 10/1998 |
| JP | 2001-172259 | 6/2001 |
| WO | WO 99/65993 | 12/1999 |
| WO | WO 00/75237 | 12/2000 |
| WO | WO 01/11373 | 2/2001 |

OTHER PUBLICATIONS

International Search Report from related foreign application No. 02253557.9–1218.

Primary Examiner—Joseph K. McKane
Assistant Examiner—Golam M M Shameem
(74) Attorney, Agent, or Firm—Knobbe, Martens, Olson & Bear, LLP

(57) ABSTRACT

A novel carbodiimide compound represented by the general formula (1) having an ester linkage and containing a fluorescent group can be prepared for providing a novel carbodiimide compound and a process for producing such a compound, in which the fluorescent group of such a compound can be efficiently introduced into a nucleic acid including a naturally-occurring nucleic acid or into a protein in a simple manner, while retaining a sufficient solubility to water. In addition, a fluorescent group-containing compound and a carbodiimide compound which can be efficiently coupled together in a simple manner.

3 Claims, No Drawings

FLUORESCENT GROUP-CONTAINING CARBODIIMIDE COMPOUND AND PROCESS FOR PRODUCING THE COMPOUND

This application claims priority of Japanese Patent Application No. 2001-164905, filed May 31, 2001 and Japanese Patent Application No. 2002-95074, filed Mar. 29, 2002.

BACKGROUND OF THE INVENTION

1. Field of the Invention

The present invention relates to a novel fluorescent group-containing carbodiimide compound and a process for producing the compound. More specifically, the present invention relates to a fluorescent group-containing carbodiimide compound, which is capable of efficiently introducing a fluorescent group into a nucleic acid or a protein in a simple manner, and to a process for producing the compound through which a fluorescent group can be efficiently coupled to a carbodiimide compound in a simple manner.

2. Description of the Related Art

As a method of introducing a fluorescent substance into a nucleic acid, several methods are known in the art, for example, a method of introducing a fluorescent substance into a nucleic acid using a fluorescent substance-bound nucleotide with the aid of an enzyme or the like (JP-A-6-271599); a method of biding a fluorescent substance-bound streptavidin to a biotin-labeled nucleic acid; and a method of reacting a fluorescent substance containing an amino reactive group with an amino linker-bound nucleic acid. In addition to those methods, there are known a method that utilizes a fluorescent group-containing carbodiimide compound indicative of an extremely high reactivity to a nucleic acid base (JP-A-10-287870), and the like.

Of those, however, the method disclosed in JP-A-6-271599, the method using the biotin label, and the method using the amino linker binding have disadvantages in that the fluorescent substances cannot be introduced into a naturally-occurring nucleic acid, and complicated operation is required. In the method (disclosed in JP-A-10-287870) in which a fluorescent group-containing carbodiimide compound is used, the presence of a quaternary ammonium in the molecule provides the comparatively favorable solubility to water. However, there may be cases where, in case of introducing a carbodiimide group into a polycyanine compound, the method of JP-A-10-287870 suffers a problem of difficulty. Thus, there is a need to newly investigate a simplified synthesis method.

SUMMARY OF THE INVENTION

The present invention has been made under the above-mentioned circumstances, and therefore, has an object to provide a novel fluorescent group-containing carbodiimide compound, by which fluorescent group can be efficiently introduced into a nucleic acid including a naturally-occurring nucleic acid and also efficiently introduced into a protein in a simple manner, while retaining sufficient solubility to water.

Another object of the present invention is to provide a method, which is appropriate to the manufacture of the fluorescent group-containing carbodiimide compound, and more specifically to a process for producing a fluorescent group-containing carbodiimide compound, with which a fluorescent group-containing compound and a carbodiimide compound are efficiently bound together in a simple manner.

For solving the above-mentioned problems in the art, the inventors of the present invention have conducted intensive investigation for solving the above-mentioned problems, and finally found out a fluorescent group-containing carbodiimide compound having a chemical structure with an ester linkage, represented by the following formula (1).

Thus, the present invention is following:

(1) There is provided a fluorescent group-containing carbodiimide compound, comprising a chemical structure with an ester linkage, represented by the general formula (1):

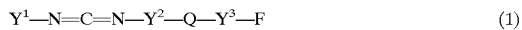

wherein each of $Y^1$, $Y^2$, and $Y^3$ is a functional group selected from the group consisting of $-CH_2-$, $-NHCO-$, $-CONH-$, $-O-$, $-S-$, $-NR^1-$ ($R^1$ is a straight-chain, circular, or branched saturated or unsaturated aliphatic hydrocarbon group having from 1 to 20 carbon atoms), $-NR^2R^3-$ ($R^2$ and $R^3$ are independently a hydrogen atom, a straight-chain, circular, or branched saturated or unsaturated aliphatic hydrocarbon group having from 1 to 20 carbon atoms, or a cycloalkyl group, an aryl group, or an aralkyl group, each of which may have a substituent, or if either $R^2$ or $R^3$ is a hydrogen atom, then the remainder is a straight-chain, circular, or branched saturated or unsaturated aliphatic hydrocarbon group having from 1 to 20 carbon atoms, or a cycloalkyl group, an aryl group, or an aralkyl group, each of which may have a substituent, and furthermore, $R^2$ and $R^3$ may be coupled together to form a nitrogen-containing heterocyclic group which may include oxygen as a whole), $-COO-$, $-OCO-$, $-NHSO_2-$, $-NHC(S)NH-$, $-SO_2NH-$, and other functional groups represented by the general formula (2):

(where L is a functional group selected from the group consisting of $-CH_2-$, $-NHCO-$, $-CONH-$, $-O-$, $-S-$, $-NR^1-$, $-NR^2R^3-$, $-COO-$, $-OCO-$, $-NHSO_2-$, $-NHC(S)NH-$, and $-SO_2NH-$; each of p and q is one of integers of from 0 to 20, while r is zero (0) or one (1), and $R^1$, $R^2$, and $R^3$ are same as those of the general formula (1));

Q is an ester linkage; and

F is a fluorescent group made of a cyanine dye represented by one of the general formulas (3-1), (3-2), and (3-3),

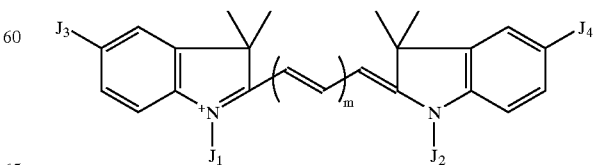

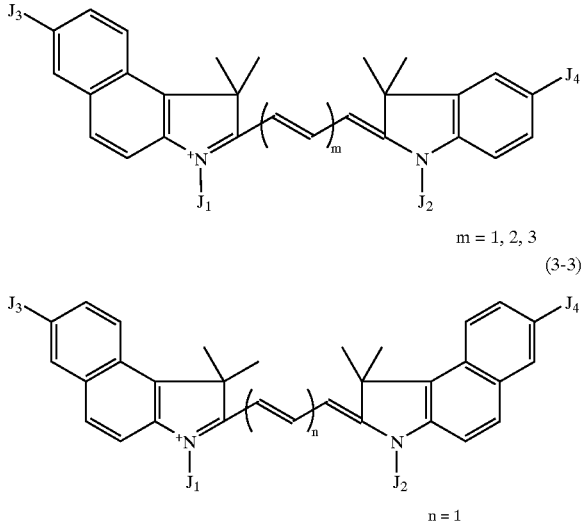

m = 1, 2, 3

(3-3)

n = 1

(where m is one of integers of from 1 to 3, while n is one (1), each of $J_1$, $J_2$, $J_3$, and $J_4$ is a functional group independently selected from the group consisting of H, OH, COOH, a sulfonic group, a sulfonate group, and an ester, amide, ether, alkyl, alkane, alkene, alkyne, allyl, and amino groups, and $J_1$ and $J_2$ are different functional groups) where each of the functional groups represented by $Y^1$, $Y^2$, $Y^3$, and F may include a group selected from the group consisting of carboxyl groups, sulfonyl groups, and phosphonyl groups, which are substituted with alkali metals, alkaline earth metals, or basic groups containing nitrogen or phosphorus, respectively, and also $Y^1$, $Y^2$, and $Y^3$ may be the same functional group or different functional groups.

(2) There is provided a fluorescent group-containing carbodiimide compound according to (1), in which at least one of the functional groups represented by $Y^1$, $Y^2$, $Y^3$, and F includes a group selected from the group consisting of carboxyl groups, sulfonyl groups, and phosphonyl groups, which are substituted with alkali metals, alkaline earth metals, or basic groups containing nitrogen or phosphorus, respectively.

(3) There is provided a process for producing a fluorescent group-containing carbodiimide compound according to (1) comprising the steps of: mixing a carbodiimide compound represented by the general formula (4) with a fluorescent group-containing compound represented by the general formula (5) to form an ester linkage, in which the general formula (4) is:

 (4)

(wherein $Y^1$ and $Y^2$ represent the same as those of the general formula (1), respectively, and $ZZ^1$ represents carboxylate, sulfonate, or phosphonate); and the general formula (5) is:

 (5)

(wherein $Y^3$ and F represent the same as those of the general formula (1), respectively, and X represents halogen).

(4) There is provided a process for producing a fluorescent group-containing carbodiimide compound according to (2), further comprising the steps of: selecting at least one of the carboiimide compound represented by the general formula (4) and the fluorescent group-containing compound represented by the general formula (5) so as to include a functional group which can be selected from the group consisting of carboxyl groups, sulfonyl groups, and phosphonyl groups, which are substituted with alkali metals, alkaline earth metals, or basic groups containing nitrogen or phosphorus, respectively, and reacting the carboiimide compound represented by the general formula (4) with the fluorescent group-containing compound represented by the general formula (5).

(5) There is provided a process for producing a fluorescent group-containing carbodiimide compound according to (3) or (4), in which the carbodiimide compound represented by the general formula (4) is prepared by the steps of:

(A) reacting an amine compound represented by the general formula (7) with an iso(thio)cyanate compound represented by the general formula (6) to synthesize a (thio)urea compound represented by the general formula (8),

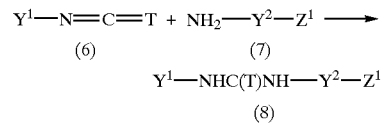

(wherein, $Y^1$ and $Y^2$ represent the same as those represented by the above-mentioned general formula (1), respectively, and T represents an oxygen atom or a sulfur atom, while $Z^1$ represents a carboxyl group, a sulfonyl group, or a phosphonium group);

(B) treating a (thio)urea compound represented by the general formula (8) with a metal or a metal salt to obtain a compound represented by the general formula (9), $Y^1$—NHC(T)NH—$Y^2$—$ZZ^1$ (9)

(wherein, $Y^1$ and $Y^2$ represent the same as those represented by the above-mentioned general formula (1), respectively, and T represents an oxygen atom or a sulfur atom, while $ZZ^1$ represents carboxylate, sulfonate, or phosphonate);

(C) obtaining a carbodiimide compound represented by the general formula (4) by subjecting the compound obtained in the step (B) represented by the above-mentioned general formula (9) to a dehydration reaction or an oxidative desulfurization reaction.

(6) There is provided a process for producing a fluorescent group-containing carbodiimide compound according to (1), comprising the steps of: mixing a carbodiimide compound represented by the general formula (10) with a fluorescent group-containing compound represented by the general formula (11) to form an ester linkage, in which the general formula (10) is:

 (10)

(wherein $Y^1$ and $Y^2$ represent the same as those of the general formula (1), respectively, and X represents halogen); and the general formula (11) is:

 (11)

(wherein $Y^3$ and F represent the same as those of the general formula (1), respectively, and $ZZ^2$ represents metal carboxylate, metal sulfonate, or metal phosphonate).

(7) There is provided a process for producing a fluorescent group-containing carbodiimide compound according to (2), further comprising the steps of: selecting at least one of the carboiimide compound represented by the general formula (10) and the fluorescent group-containing compound represented by the general formula (11) so as to include a functional group which can be selected from the group consisting of carboxyl groups, sulfonyl groups, and phosphonyl groups, which are substituted with alkali metals, alkaline earth metals, or basic groups containing nitrogen or phosphorus, respectively, and reacting the carboiimide compound represented by the general formula (10) with the fluorescent group-containing compound represented by the general formula (11).

(8) There is provided a process for producing a fluorescent group-containing carbodiimide compound according to (6) or (7), in which the carbodiimide compound represented by the general formula (10) is prepared by the steps of:

(D) reacting an amine compound represented by the general formula (13) with an iso(thio)cyanate of the general formula (12) to synthesize a (thio)urea compound (14),

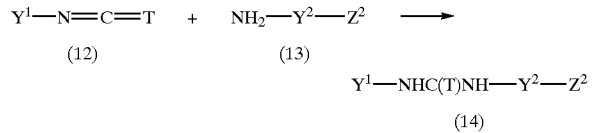

(wherein, $Y^1$ and $Y^2$ represent the same as those represented by the above-mentioned general formula (1), respectively, and T represents an oxygen atom or a sulfur atom, while $Z^2$ represents a hydroxyl group, an alkyl group, an alkenyl group, a vinyl group, an aryl group, a phenyl group, a carboxyl group, a sulfonyl group, or a phosphonium group);

(E) halogenating a (thio)urea compound represented by the general formula (14) obtained in the step (D) to obtain a compound represented by the general formula (15), $$Y^1\text{—NHC(T)NH—}Y^2\text{—X} \qquad (15)$$

(wherein, $Y^1$ and $Y^2$ represent the same as those represented by the above-mentioned general formula (1), respectively, and T represents an oxygen atom or a sulfur atom, while X represents halogen);

(F) obtaining a carbodiimide compound represented by the general formula (10) by subjecting the compound obtained in the step (E) represented by the above-mentioned general formula (15) to a dehydration reaction or an oxidative desulfurization reaction.

(9) There is provided a method of detecting an nucleic acid by a hybridization using a nucleotide labeled with a marker, in which a fluorescent group-containing carbodiimide compound according to (1) or (2) is used as the marker substance.

(10) There is provided a carbodiimide compound comprising a chemical structure represented by the general formula (4):

$$Y^1\text{—N=C=N—}Y^2\text{—ZZ}^1 \qquad (4)$$

wherein $Y^1$ and $Y^2$ represent the same as those of the general formula (1), respectively, and $ZZ^1$ represents carboxylate, sulfonate, or phosphonate.

(11) There is provided a process for producing a carbodiimide compound according to (10), in which the carbodiimide compound represented by the general formula (4) is prepared by the steps of:

(A) reacting an amine compound represented by the general formula (7) with an iso(thio)cyanate compound represented by the general formula (6) to synthesize a (thio)urea compound (8),

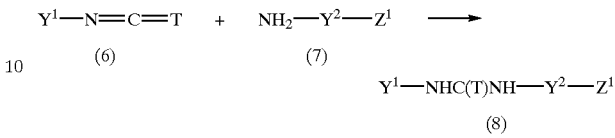

(wherein, $Y^1$ and $Y^2$ represent the same as those represented by the above-mentioned general formula (1), respectively, and T represents an oxygen atom or a sulfur atom, while $Z^1$ represents a carboxyl group, a sulfonyl group, or a phosphonium group);

(B) treating a (thio)urea compound represented by the general formula (8) obtained in the step (A) with a metal or a metal salt to obtain a compound represented by the general formula (9), $$Y^1\text{—NHC(T)NH—}Y^2\text{—ZZ}^1 \qquad (9)$$

(wherein, $Y^1$ and $Y^2$ represent the same as those represented by the above-mentioned general formula (1), respectively, and T represents an oxygen atom or a sulfur atom, while $ZZ^1$ represents carboxylate, sulfonate, or phosphonate);

(C) obtaining a carbodiimide compound represented by the general formula (4) by subjecting the compound obtained in the step (B) represented by the above-mentioned general formula (9) to a dehydration reaction or an oxidative desulfurization reaction.

DETAILED DESCRIPTION OF THE INVENTION

Hereinafter, the present invention will be described in detail. First of all, detailed description of a fluorescent group-containing carbodiimide compound of the present invention will be made.

<1> Fluorescent Group-containing Carbodiimide Compound

A fluorescent group-containing carbodiimide compound having an ester linkage in accordance with the present invention is one represented by the above-mentioned general formula (1).

In formula (1), Q represents that an ester linkage is being formed.

In formula (1), each of $Y^1$, $Y^2$, and $Y^3$ represents a functional group selected from the group consisting of —$CH_2$—, —NHCO—, —CONH—, —O—, —S—, —$NR^1$—, —$NR^2R^3$—, —COO—, —OCO—, —$NHSO_2$—, —NHC(S)NH—, —$SO_2$NH—, and other functional groups represented by the general formula (2).

$R^1$ is a straight-chain, circular, or branched saturated or unsaturated aliphatic hydrocarbon group having from 1 to 20 carbon atoms. $R^2$ and $R^3$ are independently a hydrogen atom, a straight-chain, or branched saturated or unsaturated aliphatic hydrocarbon group having from 1 to 20 carbon atoms, or a cycloalkyl group, an aryl group, or an aralkyl group, each of which may have a substituent. However, in the case where either of $R^2$ and $R^3$ is a hydrogen atom, the remainder is a straight-chain, or branched saturated or unsaturated aliphatic hydrocarbon group having from 1 to 20 carbon atoms, or a cycloalkyl group, an aryl group, or an aralkyl group, each of which may have a substituent. Further, $R^2$ and $R^3$ may be coupled together to form a nitrogen-containing heterocyclic group which may include oxygen as a whole.

Here, the nitrogen-containing heterocyclic group, which may include oxygen, may be specifically a pyridyl, pyrrolidinium, or piperidinium group, or the like.

In the above-mentioned general formula (2), L is a functional group selected from the group consisting of —CH$_2$—, —NHCO—, —CONH—, —O—, —S—, —NR$^1$—, —NR$^2$R$^3$—, —COO—, —OCO—, —NHSO$_2$—, —NHC(S)NH—, and —SO$_2$NH—. each of p and q is one of integers of from 0 to 20, while r is zero (0) or one (1). In addition, $R^1$, $R^2$, and $R^3$ are the same as those of the general formula (1).

In the general formula (1), F is a fluorescent group made of a cyanine dyne, which can be represented by any one of the above-mentioned formulas (3-1), (3-2), and (3-3).

In addition, m represents one of integers of from 1 to 3, while n represents one (1). Also, each of $J_1$, $J_2$, $J_3$, and $J_4$ is a functional group independently selected from the group consisting of H, OH, COOH, a sulfonic group, a sulfonate group, and an ester, amide, ether, alkyl, alkane, alkene, alkyne, allyl, and amino group. In this case, $J_1$ and $J_2$ each are different functional groups.

As a specific example of such a fluorescent group F, there are exemplified Cy3, Cy5, and the like which is represented by the following structural formula.

(Cy3)

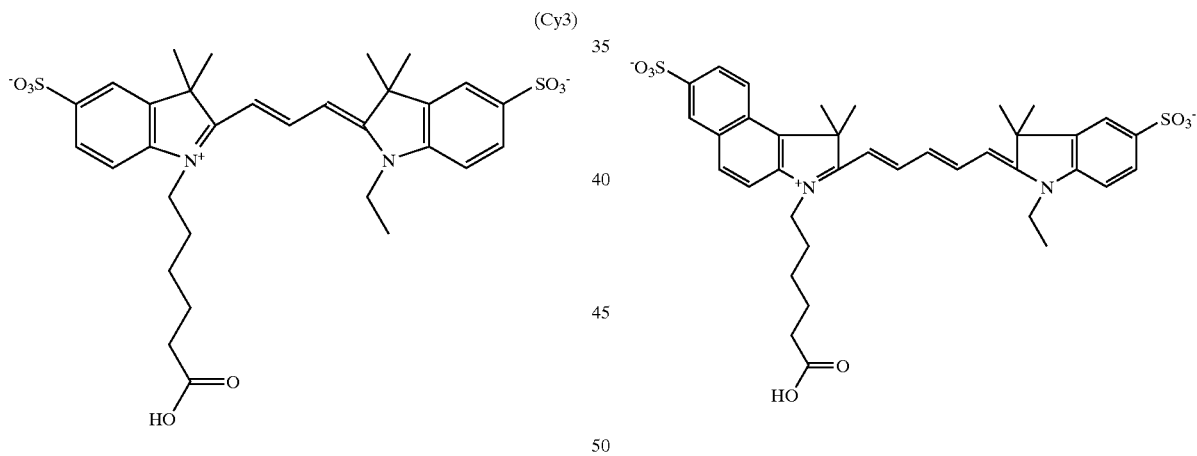

(Cy5)

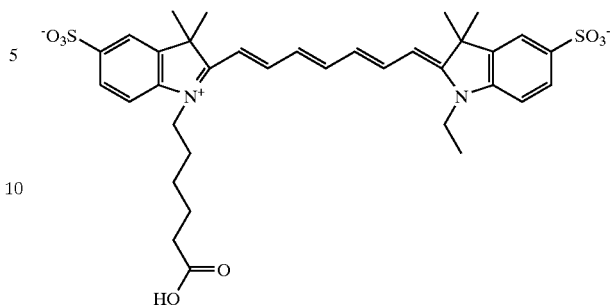

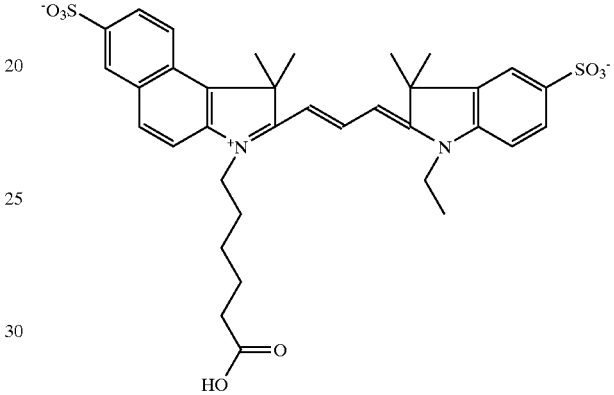

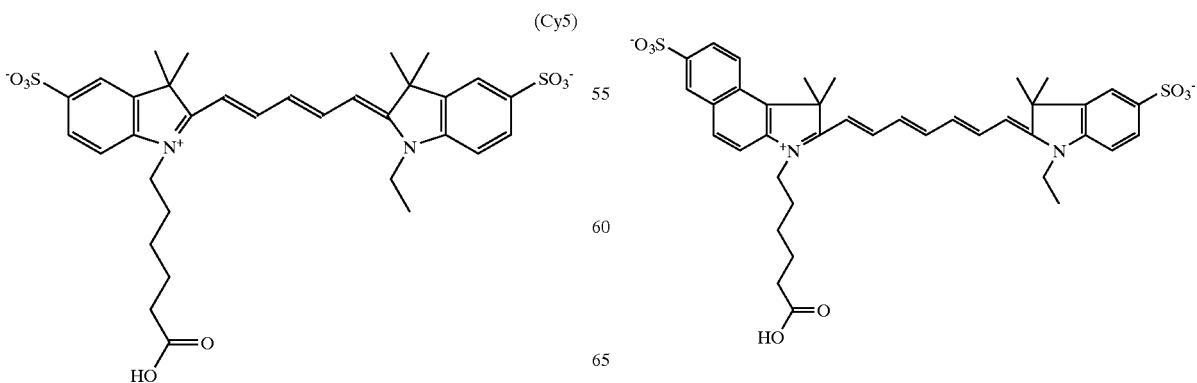

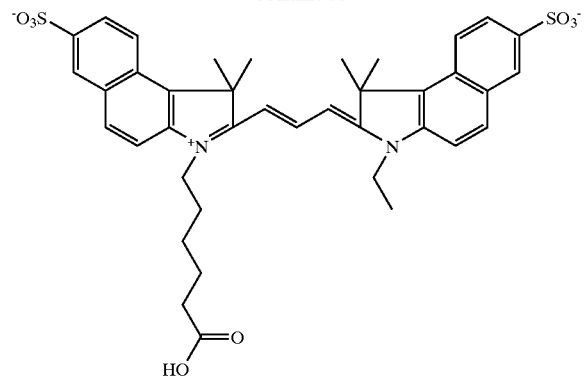

As described above, in the fluorescent group-containing carbodiimide compound represented by the general formula (1) of the present invention, each of the functional groups represented by F, $Y^1$, $Y^2$, and $Y^3$ may include a group selected from the group consisting of carboxyl groups, sulfonyl groups, and phosphonyl groups, which are substituted with alkali metals, alkaline earth metals, or basic groups containing nitrogen or phosphorus, respectively. In the present invention, preferably, at least one of functional groups to be selected from them may include at least one group selected from the group consisting of carboxyl groups, sulfonyl groups, and phosphonyl groups, which are substituted with alkali metals, alkaline earth metals, or basic groups containing nitrogen or phosphorus, respectively.

Specifically, carboxyl groups, sulfonyl groups, and phosphonyl groups, which are substituted with alkali metals, alkaline earth metals, or basic groups containing nitrogen or phosphorus, may include: —COONa, —COOK, (—COO)$_2$Mg, (—COO)$_2$Ca, (—COO)$_2$Ba, —COONH$_4$, —COONR$^1$H$_3$, —COONR$^1_2$H$_2$, —COONR$^1_3$H, —COONR$^1_4$, —SO$_3$K, —SO$_3$Na, —PO$_4$K$_2$, —PO$_4$Na$_2$, and so on (here, $R^1$ has the same meaning as that of one in the above-mentioned formula (1)).

As the specific examples of the fluorescent group-containing carbodiimide compound represented by the above-mentioned general formula (1) of the present invention, compounds represented by the following structural formulas may be included.

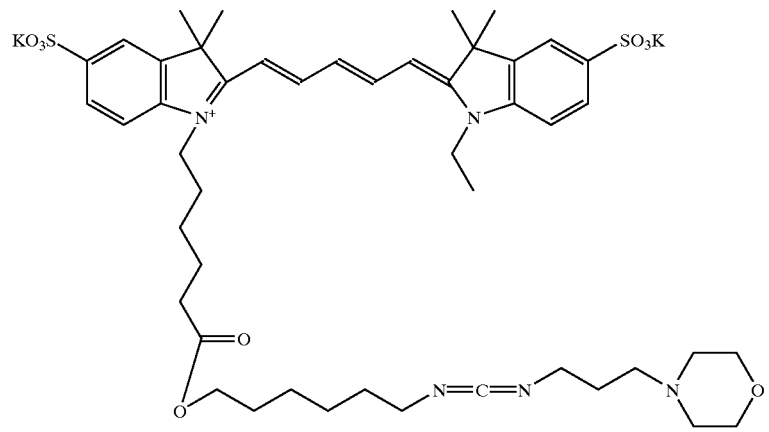

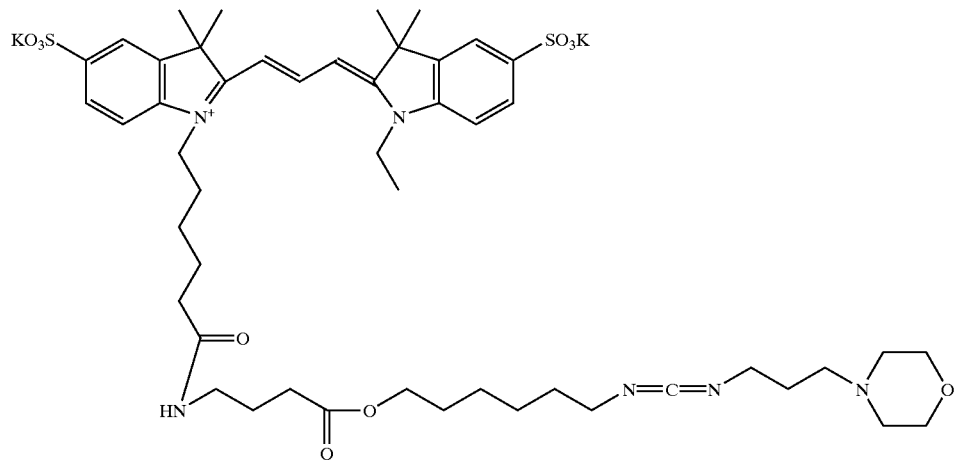

-continued

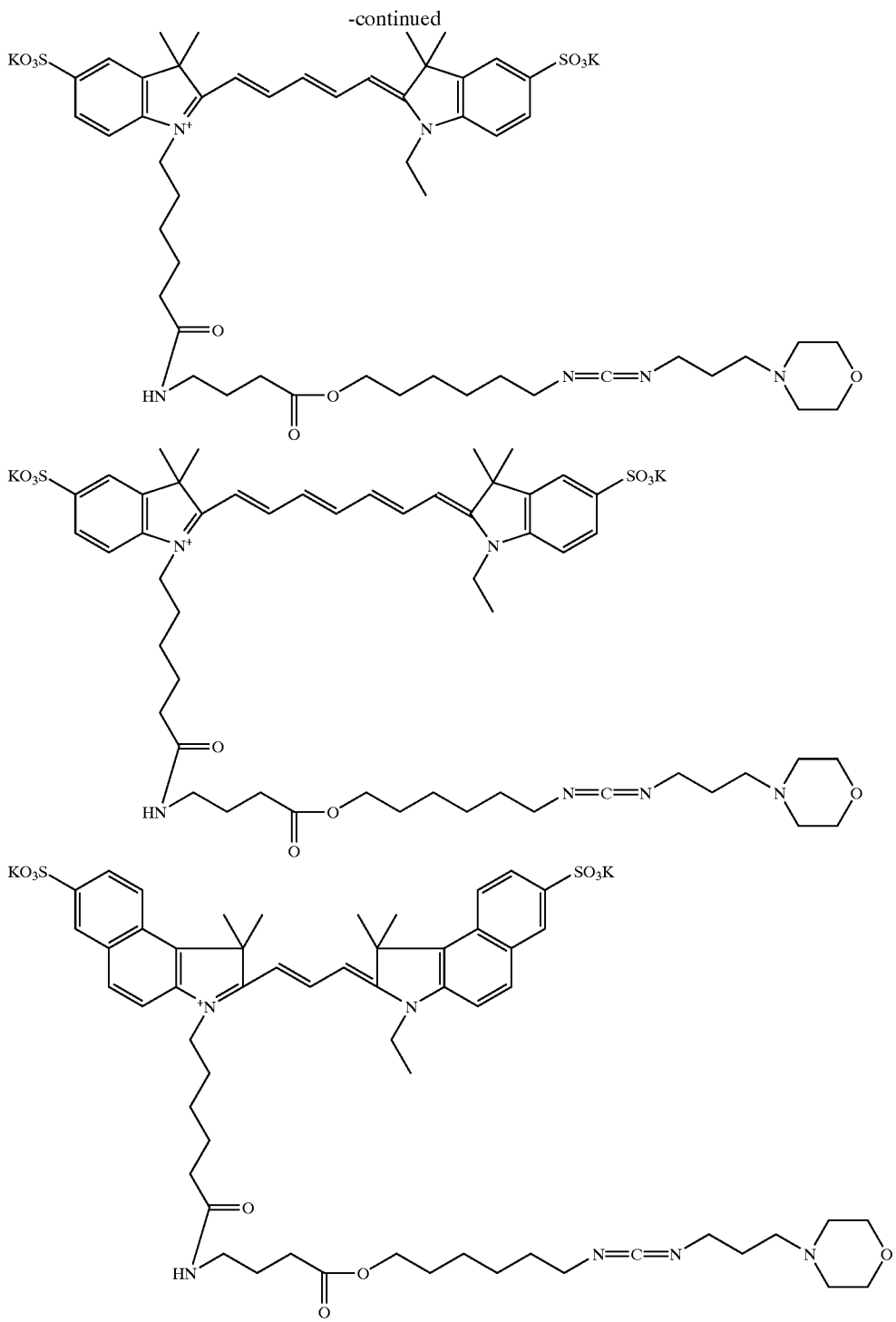

Next, description will be made of a process for producing a fluorescent group-containing carbodiimide compound according to the present invention.

<2> Process for Producing a Fluorescent Group-containing Carbodiimide Compound

According to the present invention, the process for producing a fluorescent group-containing carbodiimide compound is not particularly limited. However, there is exemplified a producing process as one of preferable embodiments of the present invention, in which a carbodiimide compound represented by the above-mentioned general formula (4) and a fluorescent group-containing compound represented by the above-mentioned general formula (5) are mixed together to form an ester linkage between the compounds.

Further, another embodiment of the producing process includes a process in which a carbodiimide compound represented by the above-mentioned general formula (10) and a fluorescent group-containing compound represented by the above-mentioned general formula (11) are mixed together to form an ester linkage between the compounds.

Now, the respective embodiments will be described below.

2-1

A fluorescent group-containing carbodiimide compound represented by the general formula (1) is prepared by mixing a carbodiimide compound represented by the above-mentioned general formula (4) with a fluorescent group-containing compound represented by the above-mentioned general formula (5) to form an ester linkage between the compounds. However, concretely speaking, the process includes the steps of: (i) preparing a carbodiimide compound represented by the above-mentioned general formula (4); (ii) preparing a fluorescent group-containing compound represented by the above-mentioned general formula (5); (iii) reacting the carbodiimide compound (4) obtained by the above-mentioned step (i) with the fluorescent group-containing compound (5) obtained by the above-mentioned step (ii) so that they are coupled together by an ester linkage, resulting in obtaining a desired fluorescent group-containing carbodiimide compound of the present invention.

Here, description will be made of each of the above-mentioned steps (i) to (iii), more concretely.

(i) The Step of Preparing the Compound Represented by the General Formula (4)

The carbodiimide compound of the present invention can be appropriately selected depending on the structure of a desired fluorescent group-containing carbodiimide compound.

In the general formula (4), $Y^1$ and $Y^2$ represent the same as those represented by the above-mentioned general formula (1), respectively. In addition, $ZZ^1$ represents carboxylate, sulfonate, or phosphonate.

The process for producing such a carbodiimide compound is not specifically limited. However, for example, it can be attained by the steps of: (A) reacting an amine compound represented by the above-mentioned general formula (7) with an iso(thio)cyanate of the above-mentioned formula (6) to synthesize a (thio)urea compound (8); (B) treating the (thio)urea compound with a metal or a metal salt, and (C) obtaining a carbodiimide compound (4) by subjecting the compound obtained in the step (B), which can be represented by the above-mentioned general formula (9), to a dehydration reaction or an oxidative desulfurization reaction. Now, description will be made of each of these steps (A) to (C) in detail.

(A) The Step of Preparing the (thio)urea Compound

Typically, an urea compound can be prepared by the reaction between an amine compound and an isocyanate compound (J. H. Saunders and R. Slocombe, Chem. Rev., 43, 203(1948)). In addition, a thiourea derivative can be also commonly prepared by the reaction between an amine compound and an isothiocyanate compound (N. A. Ivanov, R. V. Viasova, V. A. Gancharava, and L. N. Smirnov, Izv. Vyssh. Zaved. Khim. Tekhnol., 19 (7), 1010 (1976)).

The above-mentioned methods are applicable to the present invention, so that a (thio)urea compound represented by the above-mentioned general formula (8) can be prepared by reacting an iso(thio)cyanate compound represented by the above-mentioned general formula (6) with an amine compound represented by the general formula (7).

In each of the above-mentioned formulas (6) to (8), $Y^1$ and $Y^2$ represent the same as those represented by the above-mentioned general formula (1), respectively. In addition, T represents an oxygen atom or a sulfur atom, while $Z^1$ represents a carboxyl group, a sulfonyl group, or a phosphonium group.

(B) The Step of Metal or Metal Salt Treatment

Specifically, the step of metal or metal salt treatment is performed as follows.

For example, a (thio)urea compound represented by the general formula (8), which contains a carbocxyl group, is dissolved in a solvent including water, followed by the addition of an equal mole of cesium carbonate into the resulting solution to mix them together. Subsequently, the mixture is subjected to a vacuum concentration to dry it completely.

Consequently, the compound represented by the above-mentioned general formula (9) can be obtained by treating the (thio)urea compound represented by the general formula (8) with a metal or a metal salt.

In the general formula (9), $Y^1$ and $Y^2$ represent the same as those represented by the above-mentioned general formula (1), respectively. In addition, T represents an oxygen atom or a sulfur atom, while $ZZ^1$ represents carboxylate, sulfonate, or phosphonate.

(C) The Step of Dehydration or Oxidative Desulfurization

The compound represented by the general formula (9) obtained in the above-mentioned step (B) is further subjected to the reaction of dehydration or oxidative desulfurization to complete the preparation of a carbodiimide compound represented by the general formula (4) in accordance with the present invention.

Here, of the compounds of the general formula (9), the above-mentioned dehydration reaction is a reaction occurred on an urea compound in which T is oxygen. That is, it can be attained by heating the urea compound together with p-toluensulfonate chloride in the presence of a tertiary amine (G. Amiard and R. Heymers, Bull. Soc. Chim. Fr., 1360 (1956)). In the presence of quaternary ammonium, alternatively, it can be attained using p-toluensulfonate chloride and potassium carbonate (Zsuzsa M. Jaszay., Synthesis, 520 (1987)).

For obtaining the carbodiimide compound of the present invention, among the compounds of the general formula (9), the above-mentioned desulfurization reaction is occurred on a thiourea compound in which T is sulfur. In this desulfurization reaction, mercury oxide is typically used as a desulfurization agent. In addition to mercury oxide, lead oxide (F. Zetzehe and A. Fredrich, Chem. Ber., 73, 1114 (1940)), zinc oxide (R. F. Coles, U.S. Pat. No. 2,946,819 (1960)), lead carbonate, lead nitrate, lead chloride (J. C. Sheehan, U.S. Pat. No. 3,135,748(1964)), or the like can be also used. Furthermore, sodium hypochlorite may be used under alkaline conditions (H. Stetter and C. Wulff, Chem. Ber., 95, 2302(1962)).

Therefore, the carbodiimide compound represented by the general formula (4) in accordance with the present invention can be prepared as described above. However, such a method is only provided as a specific example, the order of each step is not restricted to the above-mentioned sequence of the steps.

(ii) The Step of Preparing the Fluorescent Group-containing Compound Represented by the Above-mentioned General Formula (5)

In the above-mentioned formula (5), F represents the same as that of the above-mentioned formula (1). More specifically, F is a cyanine dye represented by one represented by the above-mentioned general formulas (3-1) to (3-3). Such a cyanine dye can be prepared with reference to JP 9-325147-A (1997), JP 9-278753-A (1997), JP 10-45715-A (1998), Ratnakaer B Mujumdar et al., Bioconjugate chem., 4,2,105–111(1993), or the like.

The fluorescent group-containing compound represented by the general formula (5) is halogenated by dissolving such a compound in N,N-dimethylformamide (DMF) or the like and reacting the dissolved compound with methyltriphenoxy phosphonium iodide or the like.

(iii) The Step of Reacting the Carbodiimide Compound Obtained in the Above-Mentioned Step (i) with the Fluorescent Group-Containing Compound Obtained in the Above-Mentioned Step (ii)

A fluorescent group-containing carbodiimide compound, which can be represented by the general formula (1) in accordance with the present invention, can be prepared by reacting the carbodiimide compound represented by the general formula (4) obtained in the above-mentioned step (i) with the fluorescent group-containing compound represented by the general formula (5) obtained in the above-mentioned step (ii) such that they can be coupled together by forming an ester linkage.

Here, the ester linkage can be allowed using a method commonly used in the art, such as one using an absolute solvent (e.g., DMF) as described in S. S. Wang et al., J. Org. Chem., 42, 1286 (1997) or V. Bocchi et al., Synthesis, 961, 1979.

Moreover, in the step of preparing the fluorescent group-containing carbodiimide compound, which can be represented by the general formula (1) of the present invention, at least one of the carboiimide compound represented by the general formula (4) and the fluorescent group-containing compound represented by the general formula (5) may be selected to include a functional group which can be selected from the group consisting of carboxyl groups, sulfonyl groups, and phosphonyl groups, which are substituted with alkali metals, alkaline earth metals, or basic groups containing nitrogen or phosphorus, respectively, when the compounds are reacted with each other.

In this case, such a group selected from the group consisting of carboxyl groups, sulfonyl groups, and phosphonyl groups, which are substituted with alkali metals, alkaline earth metals, or basic groups containing nitrogen or phosphorus, respectively, may be already included in either of the carbodiimide compound represented by the general formula (4) or the fluorescent group-containing compound represented by the general formula (5) in a stage of preparing a raw material to be used. Such a group may be included in the initial stage in the producing process when the material does not contain the above-mentioned group. Alternatively, such a group may be included in an intermediate in the manufacturing process, or it may be introduced at the last when the compound represented by the general formula (4) or (5) to be finally obtained does not contain the above-mentioned group.

As a method of introducing the group into the target compound, there is a method in which a compound having a functional group for the induction and a group selected from the group consisting of a carboxy group, a sulfonyl group, and a phosphonyl group is used. Then, the carboxy group, the sulfonyl group, the phosphonyl group, or the like is converted into an alkali metal salt of sodium, potassium, or the like, or an alkaline earth metal salt such as calcium, magnesium, or the like, or a salt of the basic group including nitrogen or phosphorus, followed by introducing into the raw material, the intermediate, the final product, or the like of the carbodiimide compound or the fluorescent group-containing compound. Alternatively, the carboxyl, or sulfonyl, phosphonyl group, or the like in the above-mentioned compound may be directly introduced in the above-mentioned raw material of the precursor, the intermediate, the final product or the like without converting it into a salt form. Subsequently, the functional group may be converted into a salt form as described above.

2-2

The fluorescent group-containing carbodiimide compound of the present invention, which can be represented by the general formula (1), is prepared by mixing a carbodiimide compound represented by the above-mentioned formula (10) with the fluorescent group-containing compound represented by the above-mentioned general formula (11) so that they are coupled together to form an ester linkage. More specifically, the method includes the steps of: (i) preparing a carbodiimide compound represented by the above-mentioned general formula (10); (ii) preparing a fluorescent group-containing compound represented by the above-mentioned general formula (11); (iii) reacting the carbodiimide compound (10) obtained by the above-mentioned step (i) with the fluorescent group-containing compound (11) obtained by the above-mentioned step (ii) so that they are coupled together by an ester linkage, resulting in obtaining a desired fluorescent group-containing carbodiimide compound of the present invention. In the following description, we will explain the difference from the producing process described in the above-mentioned <2-1>.

(i) The Step of Preparing the Carbodiimide Compound Represented by the General Formula (10)

In the general formula (10), x is a halogen.

The process for producing such a carbodiimide compound is not specifically limited. However, for example, it can be attained by the steps of: (D) reacting an amine compound represented by the above-mentioned general formula (13) with an iso(thio)cyanate of the above-mentioned formula (12) to synthesize a (thio)urea compound represented by the general formula (14); (E) halogenating the (thio)urea compound; and (F) obtaining a carbodiimide compound by subjecting the compound obtained in the step (E), which can be represented by the above-mentioned general formula (15), to a dehydration reaction or an oxidative desulfurization reaction. Now, description will be made of each of these steps (D) to (F) in detail.

(D) The Step of Preparing the (thio)urea Compound

In this producing process of the present invention, the step (A) of the method (i) in the above-mentioned <2-1> can be also applicable. Typically, a (thio)urea compound represented by the general formula (14) can be prepared by the reaction between an amine compound represented by the general formula (13) and an isocyanate compound (12).

In each of the above-mentioned formulas (12) to (14), $Y^1$ and $Y^2$ represent the same as those represented by the above-mentioned general formula (1), respectively. In addition, T represents an oxygen atom or a sulfur atom, while $Z^2$ represents a hydroxyl group, an alkyl group, an alkenyl group, a vinyl group, an aryl group, a phenyl group, a carboxyl group, a sulfonyl group, or a phosphonium group.

(E) The Step of Halogenation

As a method of introducing a halogen into the (thio)urea compound represented by the general formula (14), if the hydroxyl group is introduced into the (thio)urea compound, there is a method in which the compound and a halogenation agent are mixed in a solvent known in the art, such as DMF, benzene, or pyridine, to react with each other. In this method, the halogenation agent may include hydrogen halide, sodium halide, potassium halide, a phosphorus halide, triester phosphonate halide, phosphine halide, thionyl halide, acid halogen compound, or the like (O. Kamm, C. S. Marvel, Org. Synth., 1, 25 (1941); T. A. Wnuk, P. Kovacic, J. Am. Chem. Soc., 97,5807 (1975); J. D. Bartleson, R. E. Burk, H. P. Lankelma, J. Am. Chem. Soc., 68, 2513 (1946); K. Friedlich, H. K. Thieme, Synthesis, 111 (1973); H. Stone, H. Shechter, Org. Synth., 4,323 (1963); T. H. Bevan, T. Malkin, D. B. Smith, J. Chem. Soc., 1383 (1955)).

More specifically, the above-mentioned halogenation agent may be hydrobromic acid, sodium bromide, zinc chloride, phosphorus tribromide, phosphorous trichloride, potassium iodide, triphenylphosphonate methyliodide, iodine, sodium iodide, methansulfonyl chloride, triphenylphosphine dibromide, triphenylphosphine dichloride, triphenylphosphine diiodide, thyonyl chloride, thionyl bromide, or the like.

Consequently, the compound having the above-mentioned formula (15) can be obtained by subjecting the (thio)urea compound represented by the general formula (14) to the reaction described above.

In the general formula (15), $Y^1$ and $Y^2$ represent the same as those represented by the above-mentioned general formula (1), respectively. In addition, T represents an oxygen atom or a sulfur atom, while X represents a halogen.

(F) The Step of Dehydration or Oxidative Desulfurization

The compound represented by the general formula (15) obtained in the above-mentioned step (D) is further subjected to the reaction of dehydration or oxidative desulfurization to complete the preparation of a carbodiimide compound represented by the general formula (10) in accordance with the present invention.

In this case, the method described in the (C) of the producing process (i) in the above-mentioned <2-1> can be applicable.

(ii) The Step of Preparing the Fluorescent Group-containing Compound Represented by the Above-Mentioned General Formula (11)

In the above-mentioned formula (5), $ZZ^2$ represents metal carboxylate, metal sulfonate, or metal phosphonate.

In addition, for obtaining the fluorescent group-containing compound represented by the general formula (11), the method may utilize an acid-base reaction (i.e., a method in which carboxylic acid is reacted with cesium carbonate or the like in a solvent including water). (iii) The step of reacting the carbodiimide compound obtained in the above-mentioned step (i) with the fluorescent group-containing compound obtained in the Above-Mentioned Step (ii)

A fluorescent group-containing carbodiimide compound, which can be represented by the general formula (1) in accordance with the present invention, can be prepared by reacting the carbodiimide compound represented by the general formula (10) obtained in the above-mentioned step (i) with the fluorescent group-containing compound represented by the general formula (11) obtained in the above-mentioned step (ii) such that they can be coupled together by an ester linkage between the compounds.

Moreover, in the step of preparing the fluorescent group-containing carbodiimide compound, which can be represented by the general formula (1) of the present invention, at least one of the carboiimide compound represented by the general formula (10) and the fluorescent group-containing compound represented by the general formula (11) may be selected to include a functional group which can be selected from the group consisting of carboxyl groups, sulfonyl groups, and phosphonyl groups, which are substituted with alkali metals, alkaline earth metals, or basic groups containing nitrogen or phosphorus, respectively, when these compounds are reacted with each other.

The concrete step of such a reaction is identical to that of the producing process (iii) in the above-mentioned <2-1>.

The fluorescent group-containing carbodiimide compound to be obtained by the above-mentioned method can be appropriately used as a marker in an assay for detecting a nucleic acid and an immunoassay. In such a case, the fluorescent group-containing carbodiimide compound of the present invention can be coupled to a nucleic acid of DNA or the like, or a protein of antigen, antibody, or the like when they are contact with each other by mixing them in an appropriate solvent, or the like. That is, a high-reactive carbodiimide group in the fluorescent group-containing carbodiimide compound of the present invention is coupled to the nucleic acid or the protein, so that a fluorescent substance to be effected as a high-sensitive detection agent can be added to the nucleic acid or the protein, resulting in the labeled product. Therefore, for coupling between the fluorescent group-containing carbodiimide compound and the nucleic acid or the protein, it is preferable that they are contact with each other under alkaline conditions (e.g., approximately pH 7.5–8.5). Furthermore, the fluorescent group-containing carbodiimide compound of the present invention can be also applicable to a chemiluminescence analysis or the like.

Moreover, as another preferred embodiment, the fluorescent group-containing carbodiimide compound has at least one of the functional groups $Y^1, Y^2, Y^3$, and F of the general formula (1) which is selected from the group consisting of carboxyl groups, sulfonyl groups, and phosphonyl groups, which are substituted with alkali metals, alkaline earth metals, or basic groups containing nitrogen or phosphorus, respectively. In this case, a carbodiimide group of the fluorescent group-containing carbodiimide compound is in the same system as that of a salt of the functional group such as a carboxyl, sulfonyl, or phosphonyl group, so that the water solubility is improved, compared with the conventional fluorescent group-containing carbodiimide compound. Therefore, the fluorescent carbodiimide of the present invention is advantageous to be used as a marker of the assay for detecting a target nucleic acid or the immunoassay, or used in the chemiluminescence analysis or the like.

<3> Method of Detecting a Nucleic Acid in Accordance with the Present Invention

The fluorescent group-containing carbodiimide compound having an ester linkage of the present invention can be used as a marker in an assay for detecting a nucleic acid by a hybridization using a marker-labeled nucleic acid. That is, the nucleic acid labeled with the fluorescent group-containing carbodiimide compound can be used as a hybridization probe. A target nucleic acid is hybridized with the probes to form hybrids between the target nucleic acid and the labeled nucleic acid. Subsequently, free probes are removed from the system, followed by measuring the amount of markers included in the hybrids to detect the presence of the target nucleic acid. In the present invention, the fluorescent group-containing carbodiimide compound can be directly detected by the measurements of fluorescent intensities or the like using a spectrofluorometer, a spectrofluorometer for 96-well microtiter plate, a fluorescence microscope, or the like. The target nucleic acid is generally fixed on any film such as a nylon membrane or a nitrocellulose, or a microtiter plate.

A hybridization used in the assay for detecting the target nucleic acid in accordance with the present invention is not restricted to specific one. It may be any conventional hybridization of the nucleic acid, except of using the fluorescent group-containing carbodiimide compound as a probe marker, such as colony hybridization, plaque hybridization, dot-blot hybridization, Southern hybridization, Northern hybridization, or the like. The target nucleic acid may be DNA or RNA, and also the nucleic acid to be used as a probe may be also DNA or RNA.

The nucleic acid to be used as a probe may be preferably prepared by labeling a polynucleotide or an oligonucleotide using the above-mentioned method. Alternatively, it may be attained by incorporating the labeled nucleotide into the polynucleotide or the poligonucleotide by a polymerase reaction.

The above-mentioned fluorescent group-containing carbodiimide compound of the present invention has a sufficient solubility to water and allows an efficient introduction of a fluorescent group into a nucleic acid or a protein in a simple manner.

EXAMPLES

Hereinafter, description will be made of the present invention in more detail by way of the concrete examples.

Example 1

(1) Carbodiimide Compound Represented by the General Formula (10) was Prepared 1.68 g (10 mmol) of N-(3-morpholinopropyl) isothiocyanate (12-1) was dissolved in 15 ml of dried methylene chloride and was then cooled in an ice bath. Subsequently, 1.17 g (10 mmol) of 6-aminohexanol (13-1) was added in the mixture, followed by stirring overnight at a room temperature. Then, water was added in the reaction mixture, followed by an extraction using methylene chloride. The resulting product was dried using anhydrous magnesium sulfate. Then, the dried product was filtrated using cerite and condensed, resulting in 2.7 g (95% in yield) N-(3-morpholinopropyl)-N-(hexane-6-ol)-thiourea (14-1) as a final product. The resulting compound was subjected to a NMR spectroscopy and the following NMR spectrum data was obtained.

$^1$H-NMR(CDCl$_3$):δ=1.35–1.85(m,12H), δ=2.40–2.60(m, 6H), δ=3.45(br,2H), δ=3.65(t,2H), δ=3.75(t,4H)

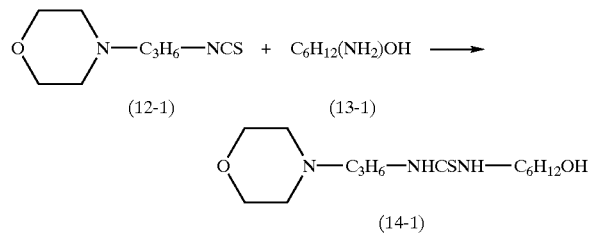

(12-1)  (13-1)

(14-1)

Next, 2 g (3.62 mmol) of the thus-obtained N-(3-morpholinopropyl)-N-(hexane-ol)-thiourea (14-1) was dissolved in 5 ml of dimethylformamide (DMF) and 3.27 g (7.23 mmol) of methyl-(triphenyl)-hosphonium iodide was then added, followed by stirring for 3 hours at a room temperature. Then, 5 ml of methanol was added and the mixture was further stirred for 20 minutes. Furthermore, the reaction mixture was condensed and was then isolated and purified by silicagel chromatography (eluent: chloroform/methanol=50/1), resulting in 2.98 g (95% in yield) of N-methyl-(3-morpholinopropyl)-N-(hexane-6-iodide)-S-methylthiourea (15-1) as a final product. The resulting compound was subjected to a NMR spectroscopy and the following NMR spectrum data was obtained.

$^1$H-NMR(CDCl$_3$):δ=1.30–1.90(m,10H), δ=2.25(t,2H), δ=2.85–3.00(m,6H), δ=2.95(s,3H), δ=3.20(t,2H), δ=3.45 (br,2H), δ=3.90(t,4H)

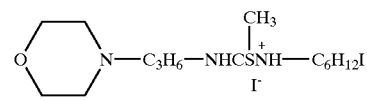

(15-1)

Subsequently, 2 g (2.31 mmol) of the thus-obtained N-methyl-(3-morpholinopropyl)-N-(hexane-6-iodide)-S-methylthiourea was dissolved in 5 ml of acetone and 1 g (4.62 mmol) of zinc oxide was then added little by little, followed by stirring for 3 hours at reflux. Then, the reaction mixture was cooled by being left standing for a hour. Subsequently, the cooled mixture was condensed by decantation, resulting in 1.73 g (90% in yield) of N-(3-morpholinopropyl)-N-(hexane-6-iodide)-carbodiimid e (10-1) as a final product. The resulting compound was subjected to a NMR spectroscopy and the following NMR spectrum data and IR spectrum data were obtained, respectively.

$^1$H-NMR(CDCl$_3$):δ=1.30–1.90(m, 10H), δ=2.40–2.50(m, 8H), δ=3.15(s,3H), δ=3.20(t,2H), δ=3.30(t,4H), δ=3.75(t, 4H)

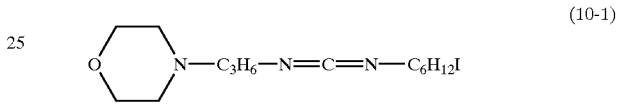

(10-1)

(2) Fluorescent Group-containing Compound Represented by the General Formula (11) was Prepared 200 mg (0.175 mmol) of Cy3.29.OSu manufactured with reference to JP-A-9-325147 and Ratnakaer B Mujumdar et al., Bioconjugate chem., 4, 2, 105–111 (1993) was dissolved in 5 ml of DMF and 164 mg (0.698 mmol) of 1-aminopropionate cesium salt was then added, followed by stirring for 12 hours at a room temperature. Subsequently, the reaction mixture was condensed after filtration and ethyl acetate/methanol was then added, followed by repeating decantation several times, resulting in 195 mg of a compound (11-1) (87% in yield) as a final product. The resulting compound was subjected to a NMR spectroscopy and the following NMR spectrum data was obtained.

$^1$H-NMR(DMSO):δ=1.30–1.60(m,12H), δ=1.70(s,12H), δ=2.05(t,4H), δ=2.10–2.30(m,8H), δ=2.15(s,12H), δ=2.95 (q,4H), δ=4.12(t,4H), δ=6.54(d,2H), δ=7.36–7.95(m,6H), δ=8.36(t,1H)

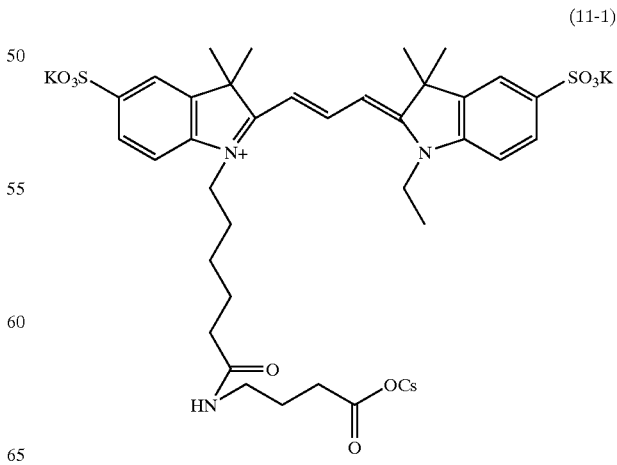

(11-1)

(3) Fluorescent Group-Containing Carbodiimide Compound Represented by the General Formula (1) was Obtained 79 mg (0.152 mmol) of the compound (10-1) obtained by the above-mentioned process (1) and 194 mg (0.152 mmol) of the compound (11-1) obtained by the above-mentioned process (2) were dissolved in 10 ml of DMF and were then stirred overnight at a room temperature, followed by a gel filtration. Subsequently, ethyl acetate/methanol was added in the mixture, followed by decantation, resulting in 189 mg (89% in yield) of a compound (1-1) as a fluorescent group-containing carbodiimide compound of the present invention. The resulting compound was subjected to a NMR spectroscopy, an IR spectroscopy, and a UV spectroscopy and the following NMR spectrum data, IR spectrum data, and UV spectrum data were obtained, respectively.

$^1$H-NMR(DMSO):δ=1.10–1.80(m,24H), δ=1.70(s,12H), δ=2.05(m,4H), δ=2.10–2.30(m,8H), δ=2.15(s,6H), δ=2.72(s,3H), δ=2.85(s,3H), δ=2.85–3.50(m,12H), δ=3.55(m,4H), δ=4.12(t,4H), δ=6.54(d,2H), δ=7.36–7.95(m,6H), δ=8.36(t,1H)

IR: 2127 cm$^{-1}$ (—N=C=N— group)

UV(H$_2$O):λ$_{max}$=542 nm

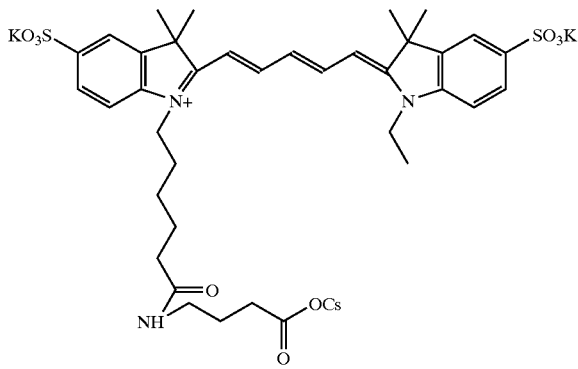

(11-2)

(2) Fluorescent Group-containing Carbodiimide Compound Represented by the General Formula (1) was Prepared 60 mg (0.157 mmol) of the compound (10-1) obtained by the above-mentioned process (1) in Example 1, and 205 mg (0.157 mmol) of the compound (11-2) obtained by the above-mentioned process (1) in Example 2 were dissolved in 10 ml of DMF and were then stirred overnight at a room

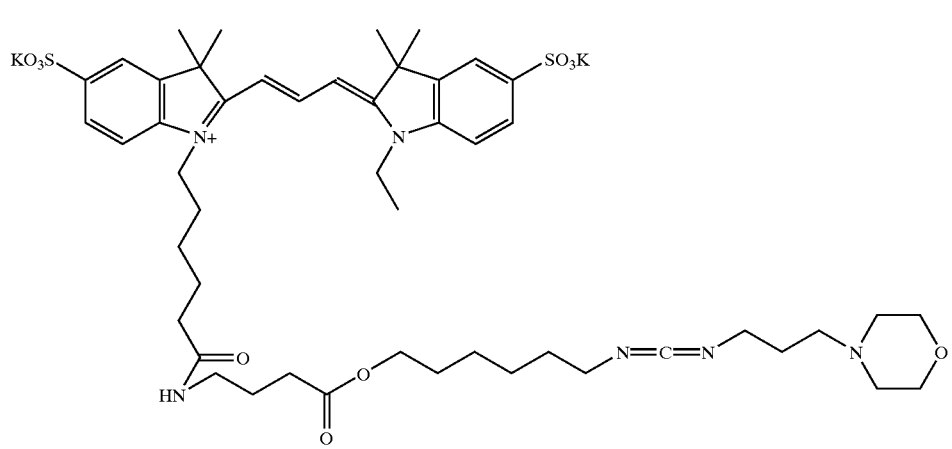

(1-1)

Example 2

(1) Fluorescent Group-Containing Compound Represented by the General Formula (11) was Prepared 200 mg (0.171 mmol) of Cy5.29.OSu manufactured with reference to JP-A-9-325147 and Ratnakaer B Mujumdar et al., Bioconjugate chem., 4, 2, 105–111 (1993) was dissolved in 5 ml of DMF and 70 mg (0.684 mmol) of 1-aminohexanoic acid cesium salt was then added little by little, followed by stirring for 12 hours at a room temperature. Subsequently, the reaction mixture was condensed and ethyl acetate/methanol was then added, followed by decantation, resulting in 184 mg (94% in yield) of a compound (11-2) as a final product. The resulting compound was subjected to a NMR spectroscopy and the following NMR spectrum data was obtained.

$^1$H-NMR(DMSO):δ=1.32–1.65(m,12H), δ=1.72(s,12H), δ=2.05(t,4H), δ=2.00–2.30(m,8H), δ=2.15(s,12H), δ=2.95(q,4H), δ=4.17(t,4H), δ=6.57(d,3H), δ=7.36–7.95(m,6H), δ=8.45(t,2H).

temperature, followed by a gel filtration. Subsequently, ethyl acetate/methanol was added in the mixture, followed by decantation, resulting in 210 mg (94% in yield) of a compound (1-2) as a fluorescent group-containing carbodiimide compound of the present invention. The resulting compound was subjected to a NMR spectroscopy, an IR spectroscopy, and a UV spectroscopy and the following NMR spectrum data, IR spectrum data, and UV spectrum data were obtained, respectively.

$^1$H-NMR(DMSO):δ=1.22–1.65(m,12H), δ=1.72(s,12H), δ=2.05(t,4H), δ=1.95–2.30(m,8H), δ=2.15(s,12H), δ=2.95(q,4H), δ=4.17(t,4H),v=6.57(d,3H), δ=7.32–7.95(m,6H), δ=8.45(t,2H).

IR: 2125 cm$^{-1}$ (—N=C=N— group)

UV(H$_2$O):λ$_{max}$=645 nm

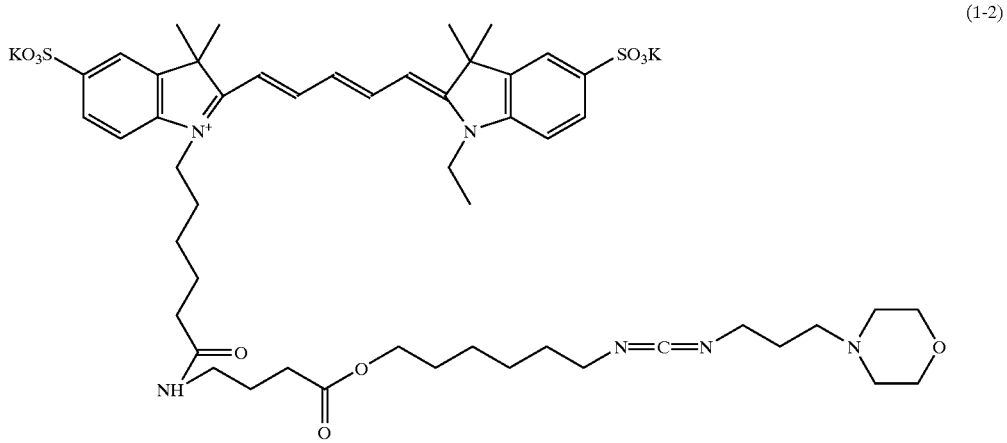

(1-2)

Example 3

(1) Fluorescent Group-containing Compound Represented by the General Formula (11) was Prepared 200 mg (0.167 mmol) of Cy7.29.OSu manufactured with reference to JP 9-325147-A and Ratnakaer B Mujumdar et al., Bioconjugate chem., 4, 2, 105–111 (1993) was dissolved in 5 ml of DMF and 161 mg (0.684 mmol) of 1-aminohexanoic acid cesium salt was then added little by little, followed by stirring for 12 hours at a room temperature. Subsequently, the reaction mixture was condensed and ethyl acetate/methanol was then added, followed by decantation, resulting in 205 mg (92% in yield) of a compound (11-3) as a final product. The resulting compound was subjected to a NMR spectroscopy and the following NMR spectrum data was obtained.

$^1$H-NMR(DMSO):δ=1.32–1.65(m,12H), δ=1.72(s,12H), δ=2.05(t,4H), δ=2.00–2.30(m,8H), δ=2.15(s,12H), δ=2.95 (q,4H), δ=4.17(t,4H), δ=6.57–8.45(m,13H).

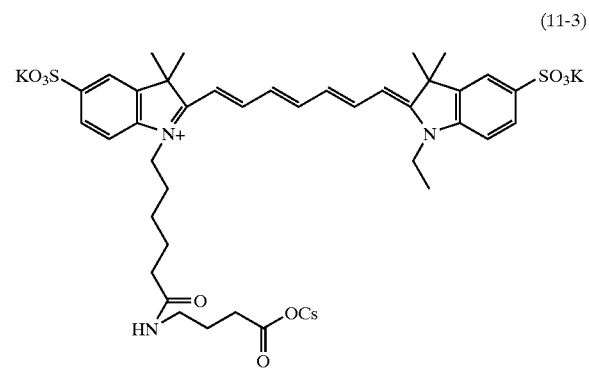

(11-3)

(2) Fluorescent Group-containing Carbodiimide Compound Represented by the General Formula (1) was Prepared 60 mg (0.157 mmol) of the compound (10-1) obtained by the above-mentioned process (1) in Example 1 and 209 mg (0.157 mmol) of the compound (11-3) obtained by the above-mentioned process (1) of Example 3 were dissolved in 10 ml of DMF and were then stirred overnight at a room temperature, followed by a gel filtration. Subsequently, ethyl acetate/methanol was added in the mixture, followed by decantation, resulting in 203 mg (89% in yield) of a compound (1-3) as a fluorescent group-containing carbodiimide compound of the present invention. The resulting compound was subjected to a NMR spectroscopy, an IR spectroscopy, and a UV spectroscopy and the following NMR spectrum data, IR spectrum data, and UV spectrum data were obtained, respectively.

$^1$H-NMR(DMSO):δ=1.22–1.65(m,12H), δ=1.72(s,12H), δ=2.05(t,4H), δ=1.95–2.30(m,8H), δ=2.15(s,12H), δ=2.95 (q,4H), δ=4.17(t,4H), δ=6.57(d,3H), δ=7.32–7.95(m,6H), δ=8.45(t,2H).

IR: 2125 cm$^{-1}$ (—N=C=N— group)

UV(H$_2$O):λ$_{max}$=745 nm (1-3)

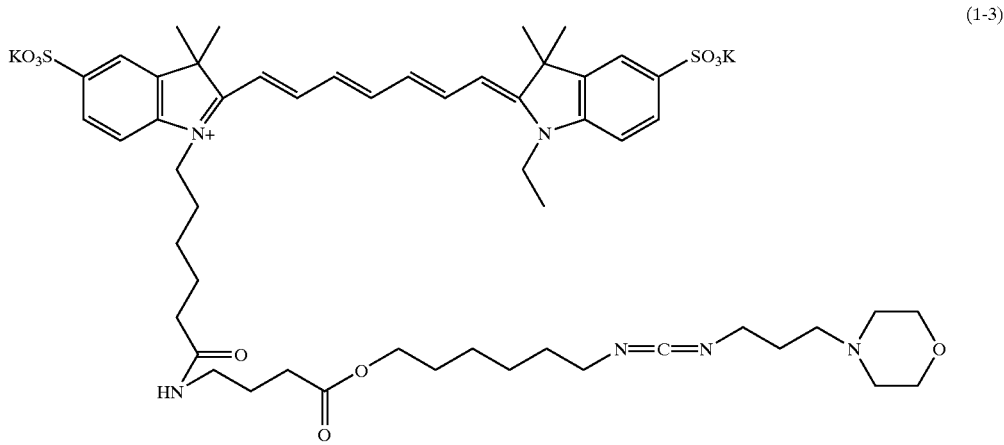

Example 4

(1) Fluorescent Group-containing Compound Represented by the General Formula (11) was Prepared 180 mg (0.167 mmol) of Cy3.5.OSu manufactured with reference to JP 9-325147-A, JP 9-278753-A, JP 10-45715-A and Ratnakaer B Mujumdar et al., Bioconjugate chem., 4, 2, 105–111 (1993) was dissolved in 5 ml of DMF and 161 mg (0.684 mmol) of 1-aminohexanoic acid cesium salt was then added little by little, followed by stirring for 12 hours at a room temperature. Subsequently, the reaction mixture was condensed and ethyl acetate/methanol was then added, followed by decantation, resulting in 205 mg (92% in yield) of a compound (11-4) as a final product. The resulting compound was subjected to a NMR spectroscopy and the following NMR spectrum data was obtained.

$^1$H-NMR(DMSO): $\delta$=1.30–1.60(m,12H), $\delta$=1.70(s,12H), $\delta$=2.05(t,4H), $\delta$=2.10–2.30(m,8H), $\delta$=2.15(s,12H), $\delta$=2.95 (q,4H), $\delta$=4.12(t,4H), $\delta$=6.54(d,2H), $\delta$=7.36–8.36(m,11H).

(11-4)

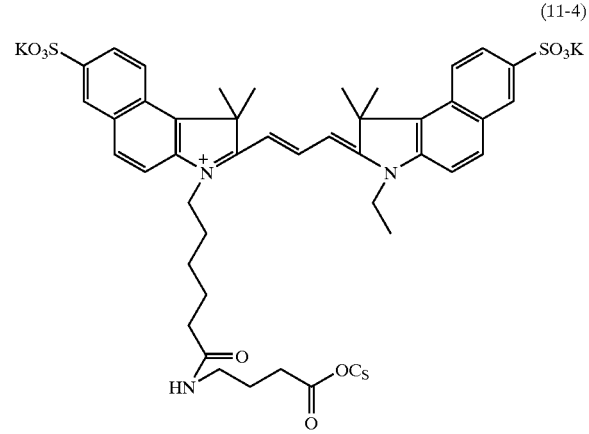

(2) Fluorescent group-containing carbodiimide compound represented by the general formula (1) was prepared 60 mg (0.157 mmol) of the compound (10-1) obtained by the above-mentioned process (1) in Example 1 and 209 mg (0.157 mmol) of the compound (11-4) obtained by the above-mentioned process (1) in Example 4 were dissolved in 10 ml of DMF and were then stirred overnight at a room temperature, followed by a gel filtration. Subsequently, ethyl acetate/methanol was added in the mixture, followed by decantation, resulting in 186 mg (89% in yield) of a compound (1–4) as a fluorescent group-containing carbodiimide compound of the present invention. The resulting compound was subjected to a NMR spectroscopy, an IR spectroscopy, and a UV spectroscopy and the following NMR spectrum data, IR spectrum data, and UV spectrum data were obtained, respectively.

$^1$H-NMR(DMSO): $\delta$=1.22–1.65(m,12H), $\delta$=1.72(s,12H), $\delta$=2.05(t,4H), $\delta$=1.95–2.30(m,8H), $\delta$=2.15(s,12H), $\delta$=2.95 (q,4H), $\delta$=4.17(t,4H), $\delta$=6.57(d,3H), $\delta$=7.36–8.36(m,11H).

IR: 2127 cm$^{-1}$ (—N=C=N— group)

UV(H$_2$O): $\lambda_{max}$=600 nm

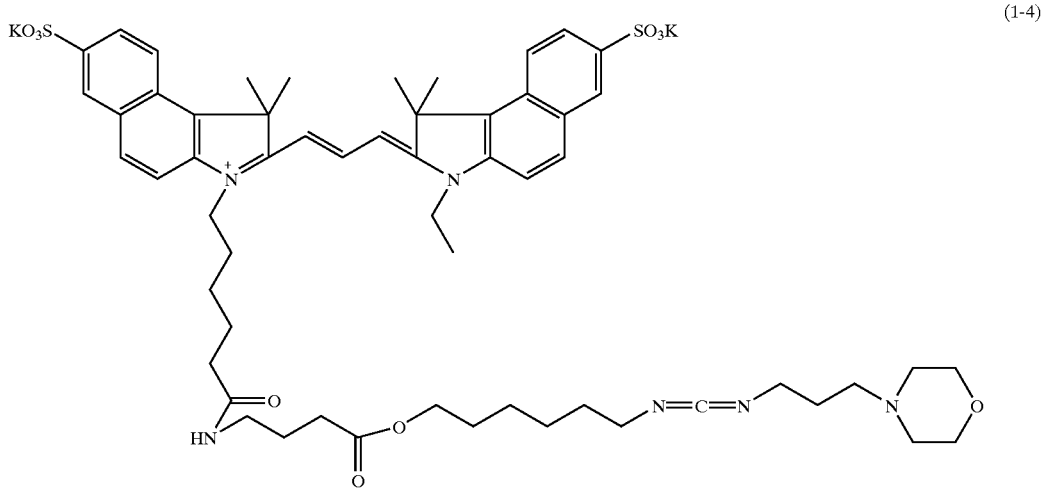

(1-4)

Example 5

A reaction solution (1 μg of phage DNA (M13mp18 replicative form: manufactured by Takara Shuzo Co., Ltd.); borate buffer (pH 8.5); and one of the compounds (1-1), (1-2), (1-3), and (1-4) obtained in the above-mentioned examples 1 to 4, respectively, at a concentration of 0.1 M) was prepared and was then incubated for 1 minute at a temperature of 85° C. Furthermore, 3M sodium acetate was added in the reaction mixture at a volume of one-ninth of the reaction mixture, while cold ethanol was also added in the reaction mixture at a volume of 2.5 times larger than that of the reaction mixture, followed by mixing them together and letting the mixture stand for 45 minutes at a temperature of −80° C. Subsequently, the mixture was centrifuged by a centrifugal machine (H-1500 FR, manufactured by a domestic manufacturer) at 12000 rpm for 1.5 minutes at a temperature of 4° C. Then, a supernatant fluid was removed and a precipitate was then dissolved in 100 μl of sterilized water.

Next, 10-fold dilution series of 480 ng to 480 pg/100 μl in 2M NaCl was prepared using the phage DNA (M13mp18 replicative form) being linearized by a restriction enzyme (HindIII), followed by the application of heat treatment for 10 minutes at a temperature of 100° C. Then, the mixture was placed on ice to rapidly cool for 5 minutes, resulting in thermal denaturation of nucleic acid. Each thermal denatured nucleic acid having respective concentrations was poured in each well of a plate and then the plate was sealed, followed by fixing for 12 hours at a temperature of 37° C.

The resulting plate in which the each sample of thermal denatured nucleic acid was fixed in each well was washed with distilled water, followed by the addition of 100 μl of pre-hybridization solution (5× SSC (1× SSC=0.15M NaCl, 0.015M sodium acid citrate), 5×denhartd's solution (0.02% polyvinylpyrrolidone, 0.2% Ficoll, 0.02% BSA), 25 mM sodium phosphate buffer (pH 6.5), 50% formamide, and 0.5 mg/ml yeast transfer RNA)) and 0.1% of dodecyl sodium sulfate solution were added. Subsequently, the mixture was agitated for 5 minutes by a plate mixer and such an agitation was repeated three times. After the agitation, the solution in each well was removed, followed by the addition of 300 μl of 2× SSC and letting it stand for 5 minutes at a room temperature.

Next, 100 μl of 50 mM sodium phosphate buffer (pH 7.0) and 1.5 M NaCl was added to each well to prepare DNA that contains a fluorescent group, i.e., each of the compounds (1-1), (1-2), (1-3), and (1-4). The solution of each well was introduced into a capillary. Then, the capillary was subjected to a spectrofluorometer (F-3010: manufactured by Hitachi, Co., Ltd.) with the radiation of an excitation light at a wavelength of 553 nm to measure 583 nm fluorescence generated from the fluorescent group labeled on the M13 replicative DNA. The obtained results are listed in Table 1.

TABLE 1

| Compound | Detection limit (ng/well) | Excitation wavelength (nm) | Fluorescent wavelength (nm) |
|---|---|---|---|
| (1-1) | 3.0 | 554 | 574 |
| (1-2) | 3.0 | 654 | 674 |
| (1-3) | 2.0 | 752 | 773 |
| (1-4) | 2.5 | 612 | 634 |

From the results described above, we confirmed that a high sensitive detection of the target nucleic acid could be attained by the nucleic-acid detection method using the fluorescent group-containing carbodiimide compound of the present invention as a marker of the detection.

What is claimed is:

1. A fluorescent group-containing carbodiimide compound, having a chemical structure with an ester linkage, represented by the general formula (1):

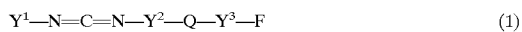

wherein
each of $Y^1$, $Y^2$, and $Y^3$ is a functional group selected from the group consisting of —$CH_2$—, —NHCO—, —CONH—, —O—, —S—, —$NR^1$— ($R^1$ is a straight-chain, circular, or branched saturated or unsaturated aliphatic hydrocarbon group having from 1 to 20 carbon atoms), —$NR^2R^3$— ($R^2$ and $R^3$ are independently a hydrogen atom, a straight-chain, circular or branched saturated or unsaturated aliphatic hydrocarbon group having from 1 to 20 carbon atoms, or a cycloalkyl group, an aryl group, or an aralkyl group, each of which may have a substituent, or if either $R^2$ or $R^3$ is a hydrogen atom, then the remainder is a straight-chain, circular, or branched saturated or unsaturated aliphatic hydrocarbon group having from 1 to 20 carbon atoms, or a cycloalkyl group, an aryl group, or an aralkyl group, each of which may have a substituent, and furthermore, $R^2$ and $R^3$ may be coupled together to form a nitrogen-containing heterocyclic group which may have an oxygen as a whole), —COO—, —OCO—, —NHSO$_2$—, —NHC(S)NH—, —SO$_2$NH—, and other functional groups selected from the functional groups represented by the general formula (2):

$$—(CH_2)_p—(L)_r—(CH_2)_q— \quad (2)$$

(where L is a functional group selected from the group consisting of —CH$_2$—, —NHCO—, —CONH—, —O—, —S—, —NR$^1$—, —NR$^2$R$^3$—, —COO—, —OCO—, —NHSO$_2$—, —NHC(S)NH—, and —SO$_2$NH—; each of p and q is one of integers of from 0 to 20, while r is zero (0) or one (1), and $R^1$, $R^2$, and $R^3$ are same as those of the general formula (1));

Q is an ester linkage; and

F is a fluorescent group made of a cyanine dye represented by one of the general formulas (3-1), (3-2), and (3-3),

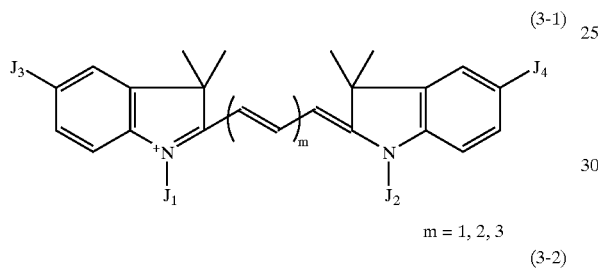

(3-1)

m = 1, 2, 3

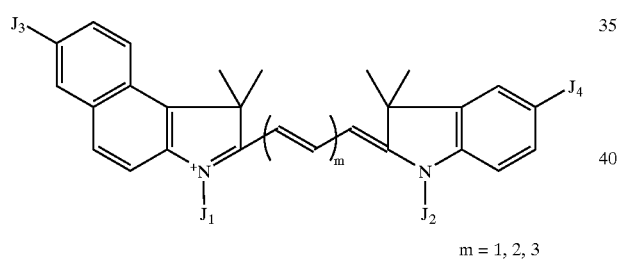

(3-2)

m = 1, 2, 3

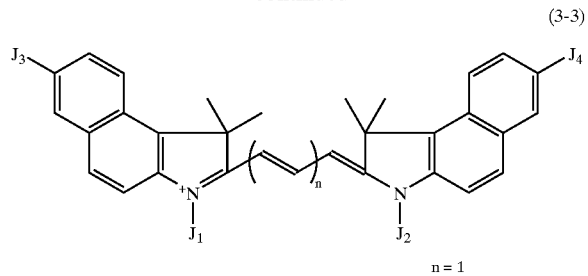

(3-3)

n = 1

(where m is one of integers of from 1 to 3, while n is one (1), each of $J_1$, $J_2$, $J_3$, and $J_4$ is a functional group independently selected from the group consisting of H, OH, COOH, a sulfonic group, a sulfonate group, and an ester, amide, ether, alkyl, alkane, alkene, alkyne, allyl, and amino groups, and $J_1$ and $J_2$ are different functional groups) where each of the functional groups represented by $Y^1$, $Y^2$, $Y^3$, and F may have a group selected from the group consisting of carboxyl groups, sulfonyl groups, and phosphonyl groups, which are substituted with alkali metals, alkaline earth metals, or basic groups containing nitrogen or phosphorus, respectively, and also $Y^1$, $Y^2$, and $Y^3$ may be the same functional group or different functional groups.

2. A fluorescent group-containing carbodiimide compound, as claimed in claim 1, wherein:

at least one of the functional groups selected from the group consisting of $Y^1$, $Y^2$, $Y^3$, and F in formula (1) having a group selected from the group consisting of carboxyl groups, sulfonyl groups, and phosphonyl groups, which are substituted with alkali metals, alkaline earth metals, or basic groups containing nitrogen or phosphorus.

3. A method of detecting a nucleic acid by a hybridization using a nucleotide labeled with a marker, wherein a fluorescent group-containing carbodiimide compound, as described in claim 1 or 2, is used as the marker substance.

* * * * *

UNITED STATES PATENT AND TRADEMARK OFFICE
CERTIFICATE OF CORRECTION

PATENT NO. : 6,825,195 B2
DATED : November 30, 2004
INVENTOR(S) : Kimura

It is certified that error appears in the above-identified patent and that said Letters Patent is hereby corrected as shown below:

<u>Column 28,</u>
Line 56, "-CONH-,-O-,-S-,-NR$^1$-" should be changed to -- -CONH-,-O-,-S-,-NR$^1$-, --.

Signed and Sealed this

Eighteenth Day of October, 2005

JON W. DUDAS
*Director of the United States Patent and Trademark Office*